(12) United States Patent
Genosar et al.

(10) Patent No.: US 8,662,349 B2
(45) Date of Patent: Mar. 4, 2014

(54) DISPENSING DEVICE INCORPORATING FRANGIBLE SECTION, ALONG WITH DISPENSING METHOD

(75) Inventors: Amir Genosar, Boulder, CO (US); Romi Genosar, Boulder, CO (US)

(73) Assignee: Aktivpak, Inc., Boulder, CO (US)

( * ) Notice: Subject to any disclaimer, the term of this patent is extended or adjusted under 35 U.S.C. 154(b) by 0 days.

(21) Appl. No.: 13/393,514

(22) PCT Filed: Aug. 30, 2010

(86) PCT No.: PCT/US2010/047187
§ 371 (c)(1),
(2), (4) Date: Jun. 13, 2012

(87) PCT Pub. No.: WO2011/026049
PCT Pub. Date: Mar. 3, 2011

(65) Prior Publication Data
US 2012/0241466 A1    Sep. 27, 2012

Related U.S. Application Data

(60) Provisional application No. 61/238,182, filed on Aug. 30, 2009.

(51) Int. Cl.
*B65D 35/28* (2006.01)

(52) U.S. Cl.
USPC ..... 222/103; 222/107; 222/541.1; 222/541.3; 222/541.6

(58) Field of Classification Search
USPC .......... 206/219, 469, 461; 604/200, 212, 214, 604/506, 310, 409, 87, 187, 416, 500, 192, 604/411, 403, 410, 905, 197, 198; 222/93, 222/94, 95, 103, 105, 107, 206, 215, 214, 222/81, 541.1, 541.2, 541.3, 541.6; 401/133, 132
See application file for complete search history.

(56) References Cited

U.S. PATENT DOCUMENTS

| 1,222,814 | A | * | 4/1917 | Storz | 604/206 |
|---|---|---|---|---|---|
| 3,192,925 | A | * | 7/1965 | Cunningham | 604/87 |
| 3,736,933 | A |   | 6/1973 | Szabo |  |
| 3,922,099 | A | * | 11/1975 | Christine et al. | 401/134 |
| 4,236,652 | A |   | 12/1980 | Beguhn |  |
| 4,430,013 | A | * | 2/1984 | Kaufman | 401/132 |
| 4,493,574 | A |   | 1/1985 | Redmond et al. |  |
| 4,724,982 | A | * | 2/1988 | Redmond | 222/94 |
| 4,790,429 | A |   | 12/1988 | Fukushima |  |
| 4,955,871 | A | * | 9/1990 | Thomas | 604/217 |
| 5,215,221 | A |   | 6/1993 | Dirksing |  |

(Continued)

FOREIGN PATENT DOCUMENTS

WO    9917821    4/1999

*Primary Examiner* — Paul R Durand
*Assistant Examiner* — Randall Gruby
(74) *Attorney, Agent, or Firm* — Perkins Coie LLP

(57) ABSTRACT

A dispensing device includes a backing, at least a first product compartment and a fluid transport device. The backing is a frangible section adapted to at least partially open as the backing is moved from a first position toward a second position. The product compartment and the fluid transport device are each disposed on the backing in confronting relationship to the frangible section. According to a method, a dispensing device is provided in which the backing is moved from the first position toward the second position to compress the first product compartment and cause the content to be dispensed through the fluid transport device.

29 Claims, 10 Drawing Sheets

(56) References Cited

U.S. PATENT DOCUMENTS

| | | | |
|---|---|---|---|
| 5,622,283 A * | 4/1997 | Morrison | 222/103 |
| 5,681,574 A | 10/1997 | Haber et al. | |
| 5,910,138 A * | 6/1999 | Sperko et al. | 604/408 |
| 6,102,896 A | 8/2000 | Roser | |
| 6,224,567 B1 | 5/2001 | Roser | |
| 6,460,781 B1 * | 10/2002 | Garcia et al. | 239/327 |
| 6,478,195 B2 * | 11/2002 | Duquet et al. | 222/183 |
| 6,585,693 B1 | 7/2003 | Dischler | |
| 6,602,222 B1 | 8/2003 | Roser | |
| 6,623,762 B2 | 9/2003 | Roser et al. | |
| 6,769,579 B2 * | 8/2004 | Milian | 222/632 |
| 6,808,507 B2 | 10/2004 | Roser | |
| 6,811,057 B2 * | 11/2004 | Duquet et al. | 222/105 |
| 6,889,870 B2 * | 5/2005 | De Laforcade | 222/1 |
| 6,932,791 B2 | 8/2005 | Taylor | |
| 7,007,831 B2 * | 3/2006 | Pennaneac'h et al. | 222/633 |
| 7,216,781 B2 | 5/2007 | Duquet et al. | |
| 7,219,874 B2 * | 5/2007 | Tippett | 251/89.5 |
| 8,403,582 B2 * | 3/2013 | Bischoff | 401/133 |
| 2004/0012135 A1 * | 1/2004 | Abergel et al. | 267/166 |
| 2005/0028813 A1 * | 2/2005 | Harrison | 128/200.22 |
| 2005/0047846 A1 * | 3/2005 | Narang et al. | 401/133 |
| 2005/0178086 A1 * | 8/2005 | Bakken | 53/412 |
| 2006/0283727 A1 * | 12/2006 | Nelson et al. | 206/219 |
| 2007/0138204 A1 * | 6/2007 | Chen et al. | 222/145.1 |
| 2008/0026066 A1 * | 1/2008 | Roser | 424/489 |
| 2008/0073372 A1 * | 3/2008 | Keller | 221/94 |
| 2008/0294100 A1 | 11/2008 | de Costa et al. | |
| 2009/0074502 A1 * | 3/2009 | Maloney et al. | 401/133 |
| 2009/0171311 A1 * | 7/2009 | Genosar et al. | 604/411 |
| 2009/0208585 A1 | 8/2009 | Roser et al. | |
| 2011/0167569 A1 * | 7/2011 | Littig et al. | 8/137 |
| 2011/0167570 A1 * | 7/2011 | Littig et al. | 8/137 |
| 2011/0170938 A1 * | 7/2011 | Littig et al. | 401/132 |
| 2012/0241465 A1 * | 9/2012 | Genosar et al. | 222/1 |

\* cited by examiner

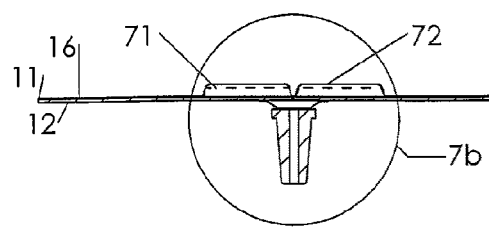
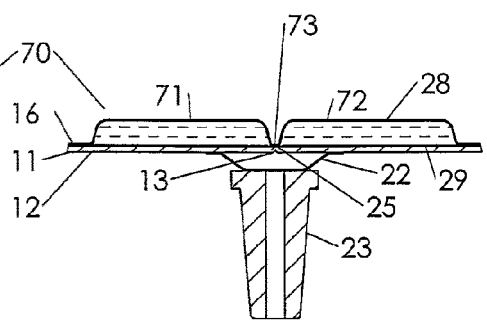
Figure 7a Figure 7b
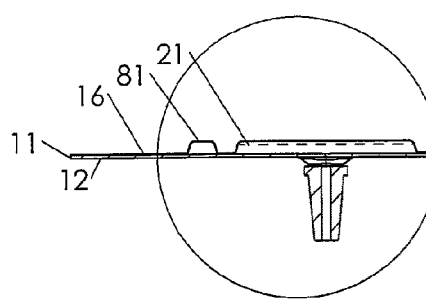
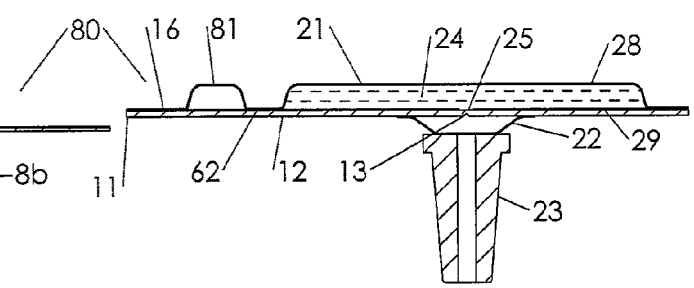
Figure 8a Figure 8b
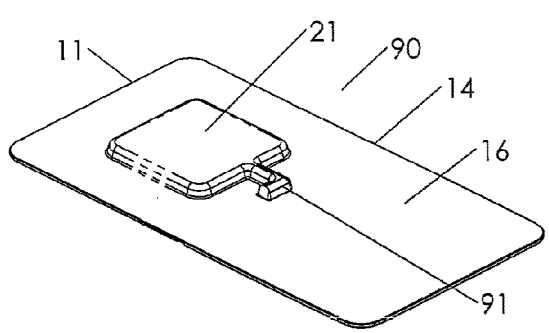
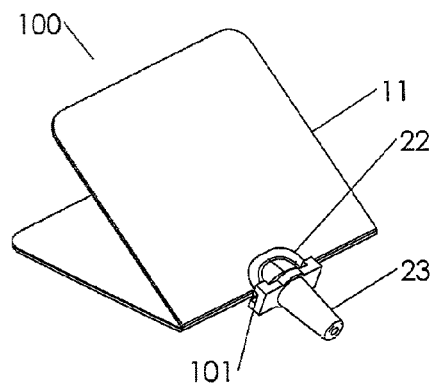
Figure 9 Figure 10

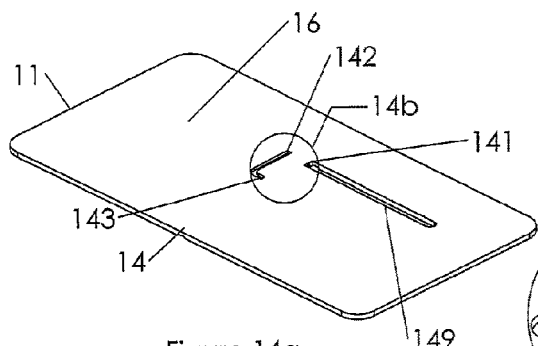
Figure 14a
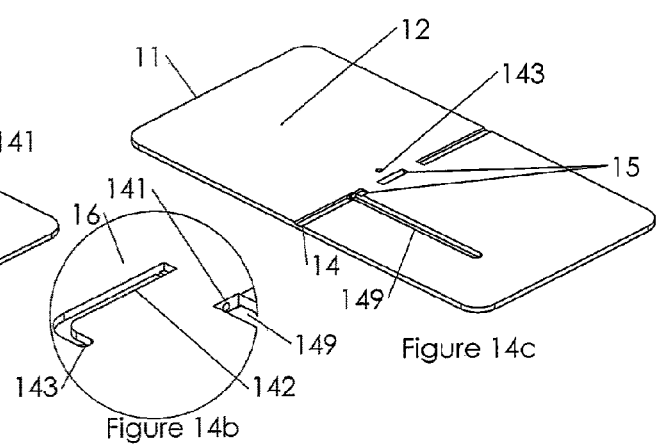
Figure 14b
Figure 14c
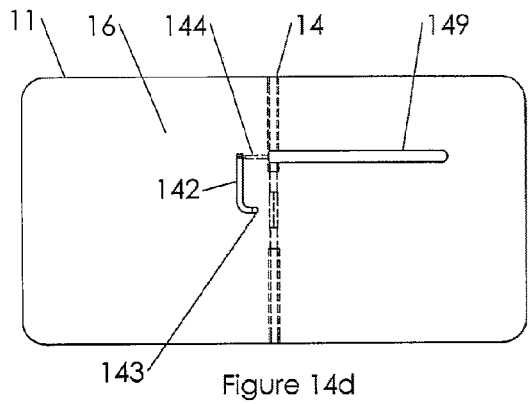
Figure 14d
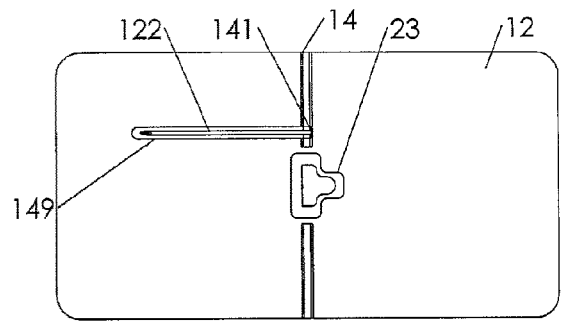
Figure 14e
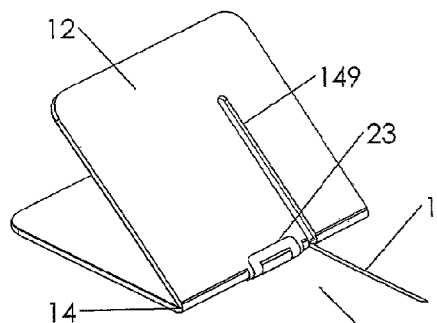
Figure 14f
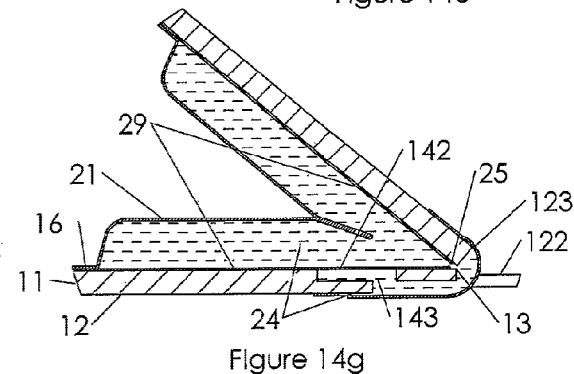
Figure 14g
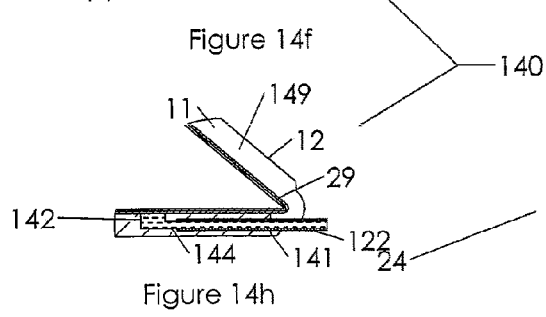
Figure 14h
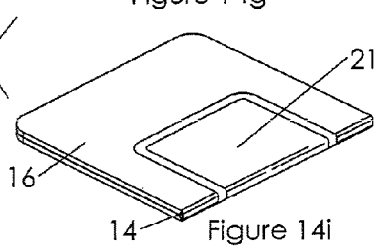
Figure 14i

DISPENSING DEVICE INCORPORATING FRANGIBLE SECTION, ALONG WITH DISPENSING METHOD

FIELD

The present invention preferably, but without limitation, generally pertains to prefilled single use, single dose dispensing packages and more specifically pertains to dispensing packages for administrations of medication.

DESCRIPTION OF THE BACKGROUND

Several commercial single dose dispensing packages include of film and/or foil (each or together hereafter sometimes referred to as "web") walls which are sealed around their edges to form a hermetically sealed compartment to store a dispensable product. These packages are commonly referred to as pouches or sachets, and are typically produced and filled using Form-Fill-Seal machines. Other single dose dispensing packages include a blow molded compartment which comprises a narrow neck for filling the content which is hermetically sealed after filling. In this application we refer to the above dispensing packages as "flexible packages". Single dose flexible dispensing packages usually comprise means for easier opening of the package without the need of applying excessive force or use of a sharp tool. These easier opening means include a slit in the edge of the package, a score across the package, or a tearable section of the package wall. Single dose flexible dispensing packages are commonly used in the beauty industry for cosmetic or perfume samples, and in the food industry for packaging a personal portion of sauce, and have the advantage of a superior barrier wall that can maintain longer shelf life for the product. One disadvantage of flexible wall packages is that they require two hand operation for opening. Another disadvantage is that the opening of the package is a ruptured wall section which does not provide quality dispensing experience in a controlled fashion, and is not designed to accept a fluid transport device for improving the dispensing quality, and the content of the package is expelled at the open edge of the package (usually smearing or flowing on the external surface of the package).

A number of commercially available single-dose flexible dispensing packages and US patents and present a special approach for opening the package. In these packages part of the package wall is a rigid and relatively brittle plastic backing that has a frangible section in form of a score or a groove such that when said backing is bent or folded this frangible section will break and allow the product to dispense. Exemplary dispensing packages that practice this approach include Donavon US Pat. Application 20060283727, Redmond U.S. Pat. No. 4,493,574, Redmond U.S. Pat. No. 4,611,715, Hoyt U.S. Pat. No. 5,316,400 DeVries U.S. Pat. No. 4,140,409; Kaufman U.S. Pat. No. 4,430,013; and Koptis U.S. Pat. No. 6,007,264 all incorporated herein by reference in their entireties. The '409 patent discloses a disposable liquid applicator including a pre-scored container such that a liquid within the applicator is dispensed into an absorbent material positioned on the exterior of the applicator at a point where the applicator snaps open when two opposing ends are bent away from the pre-scored portion.

The '013 patent discloses an applicator package with a foam applicator attached to a backing member having at least one reservoir formed of a flat sheet material for containing a material to be applied. The flat sheet material has a slit or weakened portion under the foam applicator so that, when the distal ends of the package are forced toward one another, the package ruptures along the slit or weakened portion thereby dispensing the material into the foam applicator. In addition to this embodiment, the '013 patent discloses several embodiments of the package designed for controlled dispensing and application of the material, including foam contained within the package, a "Band Aid" style opening, scrubbing bristles attached to the exterior of the package, and neck-down receptacles (similar to the design of the '409 patent).

The '264 patent to Koptis discloses a pouch-like container for dispensing ingredients via built-in outwardly pivoting flaps. In order to dispense the material within the container, the user must break apart the flaps. The pouch-like container is created and remains in a folded position.

US Pat. Application 20060283727 provides examples for constructing the device and recommended materials. The reference discusses the need for limiting the length of the rupture in the frangible wall section so as to leave smooth sections at the longitudinal ends of the backing.

What the above prior art is lacking is an approach for controlling the fashion in which the product is dispensed to enable applications that demand more than arbitrary smearing or absorption into a sponge. All of the above prior art are designed for direct application of reservoir content(s) to a surface and are not designed to direct the content exclusively to a fluid transport device, which is essential for several applications that require other types of dispensing. In addition, in the above prior art the product tends to burst out as soon as the frangible wall section breaks since the rupturing action occurs in a snap.

It is therefore a principal object of the present invention to improve upon the prior art by providing a fluid transport device for dispensing the content(s) of the package.

SUMMARY

The present disclosure overcomes the disadvantages and limitations of the prior art by providing a low cost, simple and easy to use dispensing device, preferably formed as a package, that allows the user to dispense the contents of the package in a controlled manner through a fluid transport device. As used herein, the term "fluid transport device" generally refers to any means for transporting a flowable product having at least one inlet port for introducing the product and at least one outlet port to dispense the product. Examples of fluid transport devices include a spout, a connector, a fitting, a Luer Slip connector/fitting, A Luer Lock connector, a needle, a hypodermic needle, a mini-needle, a set of mini needles, a micro needle, an array of micro needles, a tube or a pipe, a spray head, an oral dropper, a nasal dropper or sprayer, an eye dropper or sprayer, a topical applicator, a jet injector an adaptor to any of the above, an adapter to an absorbent material (such as a sponge, woven or none-woven pads, or a cloth that may be used to apply a substance to a surface such as the skin).

The present invention also overcomes the limitation of the prior art to a single-dose applications by providing means for resealing the outlet port of the package.

The present disclosure relates to a dispensing device, preferably in the form of a dispensing package, comprising a substantially flat and substantially rigid backing (or "carrier") having a fold line about which the backing can fold between a first and a second position, at least one product compartment (or "reservoir") formed on the second side of said backing for storing a product or substance of said product; a fluid transport device; and an adapter for communicating the product after opening exclusively to the fluid transport device. The present disclosure also provides means for rupturing a frangible wall of the product compartment upon folding the backing along its fold line.

US Pat. Application 20060283727 incorporated herein by reference in its entire, describes a number of basic constructions of a dispensing package, with a frangible backing, applicable for the present invention. Similar constructions are taught by US Pat. Application 20060283727 and other prior art.

The present disclosure teaches advancement to the prior art by providing a fluid transport device that communicates with the frangible wall section and receives the product and dispense it in a desired controlled fashion. To accomplish that the present invention incorporates the following features that distinguish it from the prior art: a) means for preventing that the rupture of the frangible wall section proceed beyond a designated area, b) uninterrupted surfaces surrounding the frangible section for receiving an adapter, in a fluid tight fashion, c) a fluid transport device for delivering the product in a desired controlled fashion to a target location, and d) an adapter for communicating the product between the backing and the fluid transport device.

The adapter is preferably attached to the backing around the frangible section, and the arrangement is such that the product expressed from the package is exclusively directed through the adapter to the fluid transport device. The adapter further comprises a feature for sealing to the backing around the frangible section or sections in a fluid tight fashion. In some arrangements is the adapter and the fluid transport device may be one in the same. In some arrangements, the adapter is at least partially attached to the area of the fold line of the backing and is designed to accommodate for the folding of the backing while maintaining a tight seal with the backing around the frangible wall section. For that purpose the feature of the adapter that is attached to the backing is preferably made from a flexible material such as molded, compressed, or extruded thermoplastic elastomer or from a film or foil. In some arrangement is such that the reconfiguration of the adapter when the backing is transformed from a flat configuration to a folded configuration, manipulates a piercing element that facilitates the rupture of the frangible wall section. The adapter may be attached to the backing merely around the frangible wall area. Alternatively the adapter can be attached to all or most of the backing surface. The adapter can be attached to the backing and the fluid transport device by one or more of the means known in the art including welding (heat stake, hot plate, RF, ultrasonic, IR, etc) gluing (hot glue, UV cured glue, etc.) adhesive layer of the film etc.

The fluid transport device can apply any dispensing or delivery method know in the art including: a fitting or connector including a Luer Lock fitting; a topical applicator, a dropper including for eye, ear or oral application; one or more of a needle, a mini needle or a microneedle; a spray or a squirt nozzle; and a needleless jet injector. In some arrangements the fluid transport device is fabricated from at least one injection molded plastic part, but could be made from other materials and processes as appropriate to the particular application.

The fluid transport device may further comprise a cap, a valve, a septum, a stopper or a tap for sealing the outlet port, which may be used to allow multi-dose dispensing from the package.

A one way valve (check valve) may be formed in the fluid transport device, in the adapter, or directly on the backing over the frangible wall section to avoid refill and reuse of the device.

The backing provides the platform for the device and comprises a frangible section along its fold line, and where the adapter is attached to its first side in confronting relations with the frangible section, and the package compartment or compartments is formed on its second side in confronting relations with the frangible section. Upon folding of the backing along its fold line, the frangible section is ruptured to establish the fluid communication between the first and the second side of the backing, allowing communication of the product and the fluid transport device. Numerous embodiments for forming the frangible wall section of the backing are taught in the above mentioned prior art but lack means for limiting the progression of the crack to a designated length along the fold line. In fact since the above mentioned prior art are intended for directly applying the dispensed product from the frangible section to a target surface in an uncontrolled fashion (such as merely dispensing the product to the palm or onto a sponge) it is of lesser importance for these dispensers to limit the extent of the crack of the frangible section. However, in the case of the present invention the adapter is attached to the backing around the frangible section to allow the product to exclusively flow toward the fluid transport device and therefore it is important to limit the crack in the frangible seal to a designated length and location. The present disclosure provides various configurations for accomplishing this.

BRIEF DESCRIPTION OF THE DRAWINGS

FIG. 7 illustrates a further preferred embodiment where the package comprises two substance compartments separated by a mixing seal aligned with the fold line of the backing, and wherein the substances of the compartments are mixed to form a mixed product prior to activation;

FIG. 8 illustrates a further preferred embodiment where the package comprises two substance compartments separated by a mixing seal located at an offset position from the fold line of the backing, and wherein the substances are mixed prior to activation;

FIG. 9 illustrates a further preferred embodiment where the package compartment is offset from the fold line of the backing;

FIG. 10 illustrates a further preferred embodiment where the fluid transport device comprises a yoke for fixing it to the backing during dispensing;

FIG. 14 illustrates a further preferred embodiment where the needle and the package are in fluid communication through channels in the backing;

DETAILED DESCRIPTION OF THE DRAWINGS

Figure 1A:
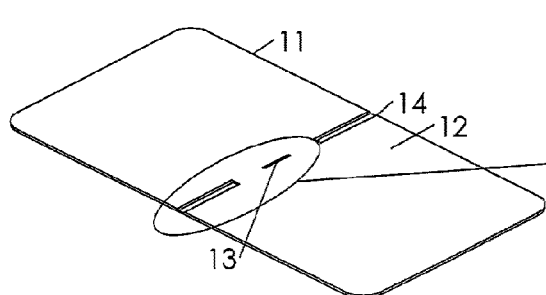
FIG. 1 illustrates a backing which may be employed in various embodiments.
Figure 1B:
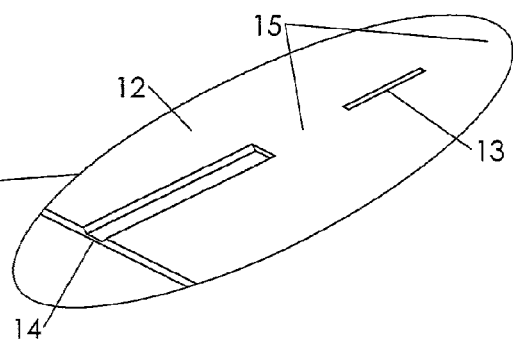
Figure 1C:
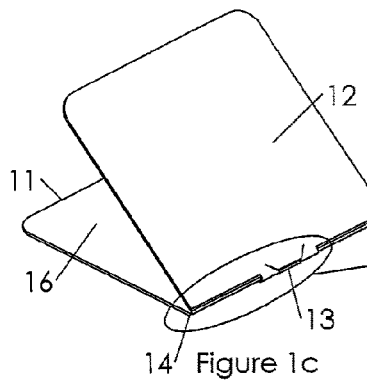
Figure 1D:
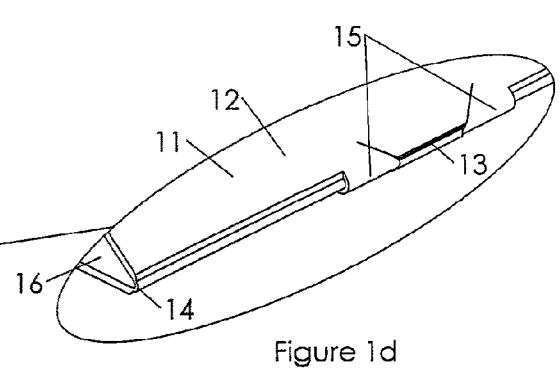

FIG. 1 illustrates a backing 11, which in configured as a panel piece, having the shape and general dimension of a credit card. FIG. 1a and detail view FIG. 1b show the first side 12 of the backing 11 which is mostly flat and comprises a thinned down sections 14 extending inwardly from a respective edge margin, defining a fold line in a form of a living hinge, and a groove 13 in line with the living hinge defining a frangible section which will break when the backing is folded. The fold line may be centrally located along the backing, separating it into first and second flaps, one of which defines a compression panel. The frangible section is continuously surrounded. FIG. 1c and the detail view FIG. 1d illustrate the backing 11 after it has been folded along the living hinge line 14. The folding can be achieved in various ways such as by one hand operation of holding the transverse edges of the backing 11 between the thumb and middle finger and pressing with the index finger against the living hinge 14 area of the first surface 12 folding of the hinge 14 causes the frangible section 13 to crack due to the strain concentration in the groove, thereby allowing fluid communication between the first side of the backing 11 and the second side of the backing 16.

The backing 11 can be produced by various techniques known in the art including plastic extrusion, plastic co-extrusion, or lamination, which is cut and embossed by stamping, compression molding, or LASER operations; metal or plastic stamping; injection molding; or a combination of the above.

Figure 1E:
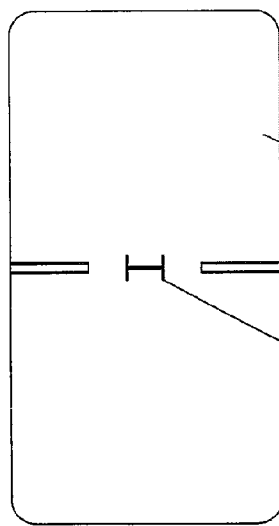
Figure 1F:
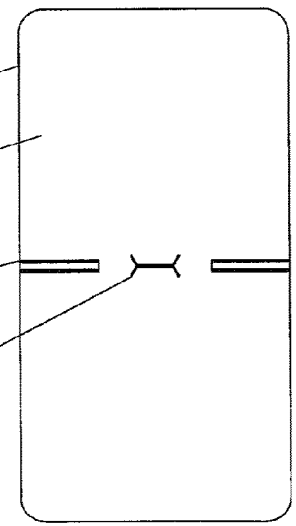
Figure 1G:
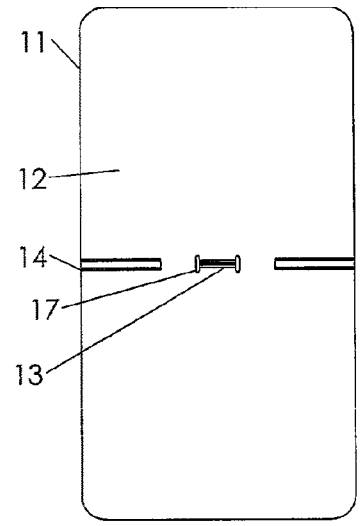

The bordering area 15 maintains a continuous smooth uninterrupted area connecting between the two flaps of the backing which is required for the functionality of the device as will be illustrated in the following Figures, and it is important to avoid the crack of frangible section 13 from progressing into the bordering area 15. FIGS. 1e, 1f and 1g illustrate different ways for achieving this.

FIG. 1e illustrates a secondary slit in addition to the primary slit in a form of v-groove sections extending transversely to the frangible section 13 thus placing boundary to the crack progression of the frangible section 13. These perpendicular grooves form a frangible seal travel limiter construction. FIG. 1f illustrates another configuration of a frangible seal travel (or progression) limiter in the form of v-grooves sections extending diagonally from the ends of the frangible wall section 13 and setting a boundary to the crack progression of the frangible section 13 as the backing 11 is folded. FIG. 1g illustrates another configuration of the frangible seal travel limiter in the form of two oval through holes 17 at the ends of frangible section 13 that set a boundary for the crack's progression as the backing 11 is folded. These various forms of the boundary features of the frangible section 13 provide a strain relief that prevent the crack of the frangible sections 13 from progressing into the bordering area 15.

Figure 1H:
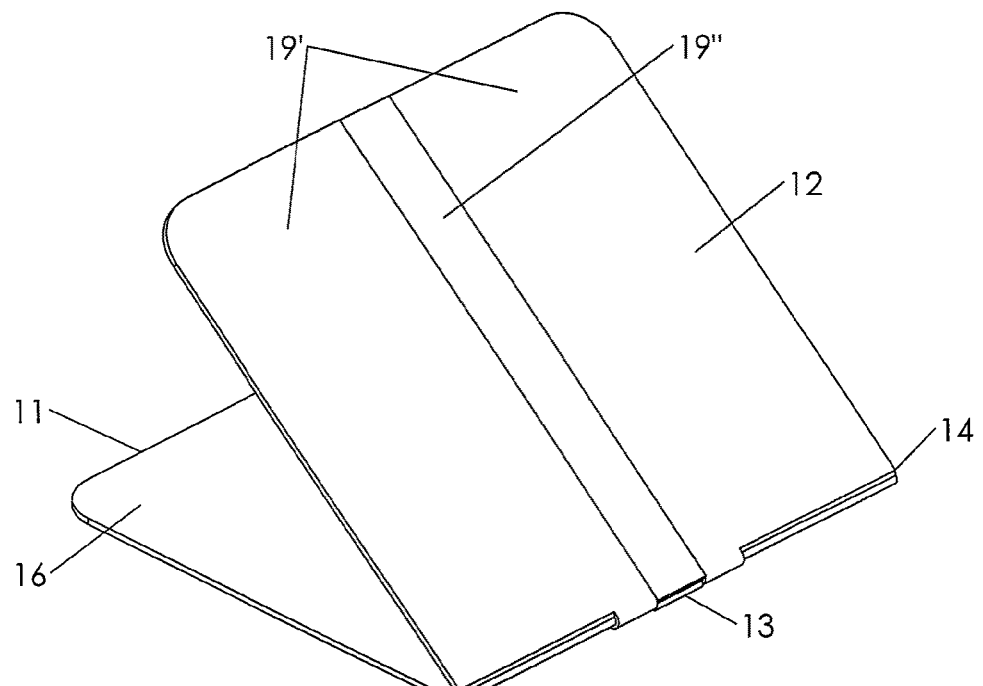
Figure 1I:
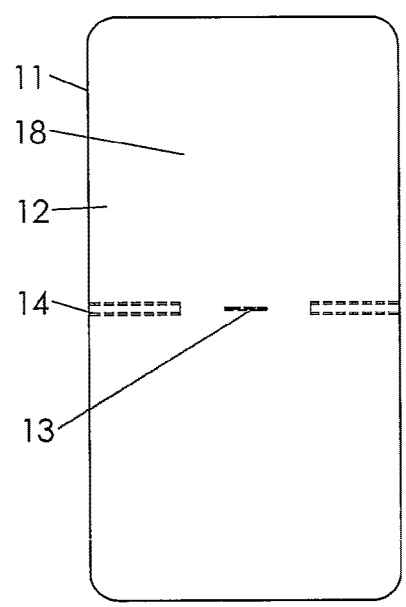

FIG. 1h illustrates another approach for limiting the progression of the crack as the backing 11 is folded. The backing 11 is produced by co-extrusion of at least two materials 19' and 19" side-by-side such that the center section 19" where the frangible wall section 13 is located is made from a first material and the side sections 19' which accommodate the bordering area 15, is made from a second material. The materials are chosen such that the material for the center section 19" is substantially brittle and tends to crack when bent while the material of the side sections 19' is more flexible and bends when the backing 11 is folded. Additional co-extruded or laminated layers may be applied over the sandwich layer described here. The backing thus comprises a first material and a second material, said first material defining said frangible section and having reduced structural integrity relative to said second material such that said first material cracks at least partially open upon movement of the backing from the first position toward the second position, while said second material remains intact FIG. 1i illustrates the backing 11 where an over-layer film lamination 18 is applied to the first side 12 of the backing 11 after the frangible section's v-groove 13 is implemented. In one embodiment the lamination 18 will rupture when the backing 11 is folded. In another embodiment the lamination 18 is ruptured by a piercing member.

FIG. 2 illustrates another embodiment 20 of the dispensing device, comprising: a backing including a frangible section adapted to at least partially open as said backing is moved from a first position toward a second position; at least a first product compartment disposed on said backing in confronting relationship to said frangible section; and a fluid transport device disposed on said backing in confronting relationship to said frangible section. FIG. 2a shows the device in a pre-activation (first) position. A product compartment 21 is constructed on the second side 16 of the backing 11 such that the compartment 21 is located on top of the frangible section 13.

Figure 2A:
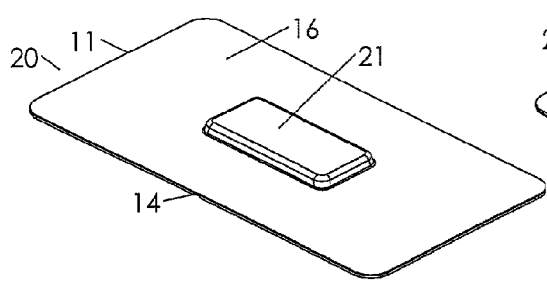
FIG. 2 illustrates a preferred embodiment having a single product compartment and where the fluid transport device is a spout connected to the backing via a flange.
Figure 2B:
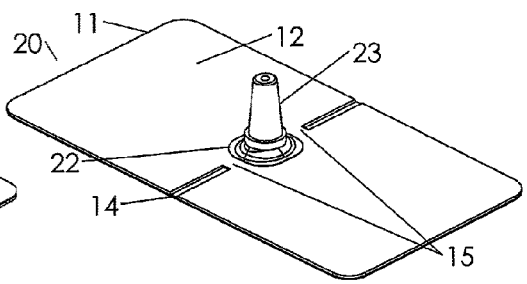

FIG. 2b shows the first side 12 of the backing 11 and a fluid transport device 23 in a fashion of a spout attached to it via a flexible adapter 22. The proximal end portion of the adapter 22 comprises a lateral flexible flange wall, sealed in a fluid-tight fashion to the bordering area 15 of the backing 11 around the frangible wall section 13. On the opposite distal end portion of the adapter 22 the frangible section 13 communicates in a fluid tight fashion to the fluid transport device 23. A through hole in the adapter 22 allows for fluid communication between the frangible section 13 and the fluid transport device 23 such that product expressed from the reservoir 21 is restricted to flow to the fluid transport device 23. The product is thus channeled through the adaptor 22.

Figure 2C:
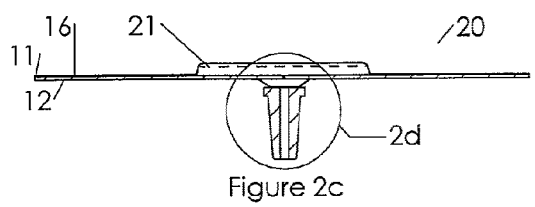
Figure 2E:
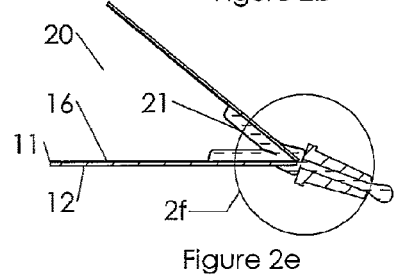
Figure 2D:
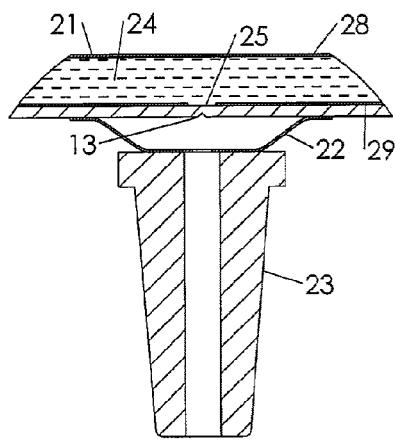

FIG. 2c and its enlarged detail view FIG. 2d show a section view of the device 20 in a flat position prior to activation. Activation refers to the state where fluid communication is established between the package and the adapter. The product compartment 21 comprises a first wall 29 attached to the second wall 16 of the backing 11, and a second wall 28. The two walls are attached to each other along their circumference in a fluid tight sealed fashion. The first wall 29 of the reservoir's compartment 21 further comprises a slit or a scoring 25 aligned with the frangible section 13. In one embodiment the scoring penetrates wall 29. In another embodiment the scoring partially cuts through the wall 29 and will rupture upon activation. The first reservoir wall 29 is attached to the second wail 16 of the backing by one of the means known in the art including lamination, adhesive, welding, mechanical clamping etc. The compartment 21 can be directly constructed on the backing 11, by: a) attaching the first wall 29 to the backing 11; b) attaching the second wall 28 to the first wall 29 around most of the circumference leaving an opening for filling the compartment; c) filling the compartment 21 with the dispensable fluid 24; and d) hermetically sealing the compartment 21. In one embodiment the compartment 21 is semi-fabricated prior to being attached to the backing 11 and filled and sealed after it has been attached to the backing 11. In another embodiment the compartment 21 is formed, filled, and sealed prior to attachment to the backing 11. The adapter is preferably face-sealed to the backing or the fluid transport device.

Figure 2F:
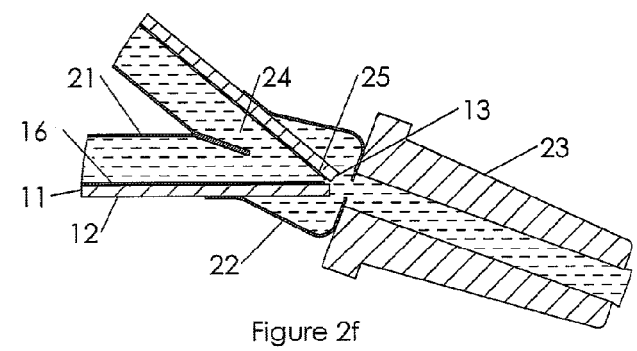

FIG. 2e and its enlarged detail FIG. 2f illustrate a section view of the device 20 in the activated position after the backing 11 has been folded along the living hinge line 14. The frangible wall section 13 is now cracked open establishing fluid communication of the product 24 between the product compartment 21 and the fluid transport device 23 via the flexible adapter 22. The flexible adapter 22 accommodates to the folded shape of the backing 11 while keeping the fluid tight connection to the backing 11 and the fluid transport device 23. The product is urged from the compartment by compressing the package between the two flaps of the backing. The product 24 will continue flowing to the fluid transport device until the backing 11 is completely folded and the compartment 21 empties (not shown).

Figure 3:
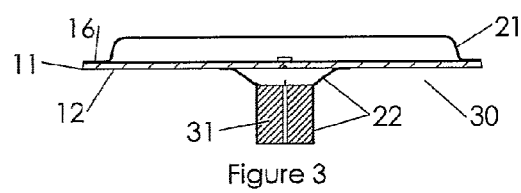
FIG. 3 illustrates an attachment of the fluid transport device to the adapter by radial sealing.

In the device 20 of FIG. 2 the connection between the backing 11 and the adapter 22 is a planar seal. FIG. 3 illustrates a further embodiment where the adapter 22 is sleeved around the fluid transport device 31.

Referring back to FIG. 2, the device 20 comprise a fluid transport device 23 in a fashion of a spout. More particularly the fluid transport device is configured in the shape of a Luer Slip male connector which can be used as a spout or as a connector in a variety of medical fluidic devices having an inlet port in a fashion of a Female Luer Slip such as a hypodermic needle hub, a Y-Connector, an infusion set, Stop-Cock etc. As noted above, various types and fashions of fluid transport devices are applicable for the present disclosure.

Figure 4:
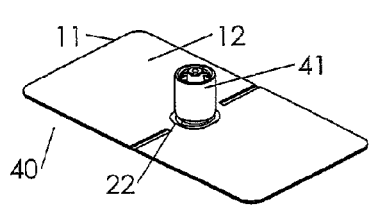
FIG. 4 illustrates the device where the fluid transport device is a Luer Lock connector.

FIG. 4 illustrates another embodiment 40 including a fluid transport device 41 in a fashion of a Luer Lock connector.

Figure 5:
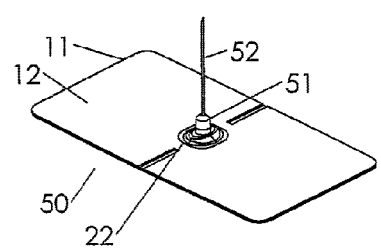
FIG. 5 illustrates the device where the fluid transport device is a hypodermic needle.

FIG. 5 illustrates another embodiment 50 including a fluid transport device 51 in a fashion of a hypodermic needle 52.

Figure 6:
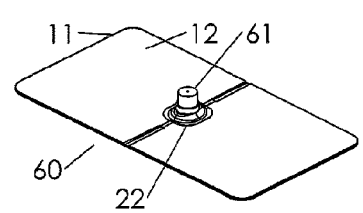
FIG. 6 illustrates the device where the fluid transport device is a spray head.

FIG. 6 illustrates another embodiment 60 including a fluid transport device 61 in a fashion of a spray nozzle.

In some embodiments the fluid transport device can be a tube, a topical applicator, an eye dropper, a nasal dispensing tip, a spoon shape receptacle for oral administration to children, etc.

FIG. 7a and its detail view in FIG. 7b illustrate a section view of a further preferred embodiment having two substance compartments 71 and 72, separated by a weak seal 73 (herein sometimes referred to as "mixing seal") forming a fluid tight separation between the compartments. At least one of the compartments 71 or 72 contains a fluidic substance while the other compartment may contain a fluid, or a solid such as a compressed solid matter, free flowing dry powder, compressed powder, powder attached to the inner side of a wall of a compartment, solid embedded on a carrier matrix, lyophilized compound, granules, etc. The mixing seal 73 is aligned with the frangible section 13 of the backing 11 and the scored section 25 of the first wall of the product compartment such that the substances in compartment 71 and 72 can not reach the scoring 25 or the frangible section 13 of the backing 11.

Prior to activating the backing 11 the two compartments are merged by rupturing the mixing seal, allowing the substances to mix and form the dispensable product. One way to rupture the mixing seal is by squeezing one or both compartments 71 or 72 thereby pressurizing the substance and forcing the mixing seal to separate. Once the frangible seal is separated the content is exposed to the scoring 25 in the first wall 29 and/or the frangible section 13 of the backing 11. The following operational steps of the device activation are similar to that described for the device 20 of FIG. 2.

FIG. 8 illustrates another preferred embodiment 80 mostly similar to the embodiment 70 of FIG. 7 with the exception that the mixing seal 62 is offset from the scoring line 25 of the first wall 29, and the frangible wall section 13 of the backing 11. This embodiment is advantageous where the volume of one compound such as in substance compartment 81) is substantially smaller than the other substance, with the intent to keep the total merged compartment substantially centered on the backing, or where the device accommodates more than two compartments.

It will be obvious to those skilled in the art that any number of compartments can be implemented. In particular, by having a plurality of compartments with aliquots of the same substance, different concentrations of the product can be formulated by the user for dispensing.

FIG. 9 illustrates a further preferred embodiment where the compartment 21 is confronting the frangible section 13, and the major part of the compartment 21 is offset from the fold line 14 of the backing 11. A thin conduit 91 formed in the wall of the compartment 21 communicates between the frangible wall section 13 of the backing 11 and the major part of the compartment 21. As a result of this arrangement, a substantially small volume of the content is displaced (squeezed) before the backing 11 has been substantially folded thus preventing an uncontrolled burst of the content immediately upon activation. This feature has particular importance where the physical setting in the dispensing position occurs subsequent to activation of the device. For example in one arrangement the fluid transport device is a needle which should be primed, piercing the skin of the patient to reduce the dead air space volume, and it is desirable to minimize the amount of product that will be expelled in that process.

Referring now to embodiment 100 shown in FIG. 10 the fluid transport device comprise a lateral protrusion 101 along the fold line 14 terminating with a yoke structure facing the fold line. When the backing 11 is folded the reconfiguration of the adapter 22 causes the fluid transport device 23 to be drawn into closer proximity to the fold line 14 where the yoke 101 mounts firmly on the folded backing, and reduces flexibility between the fluid transport device and the backing. By having the backing support both the package and the fluid transport device, a stiffer environment is created for establishing firmer communication between these components, thereby facilitating manual dispensing of the product by the user.

Figure 11A:
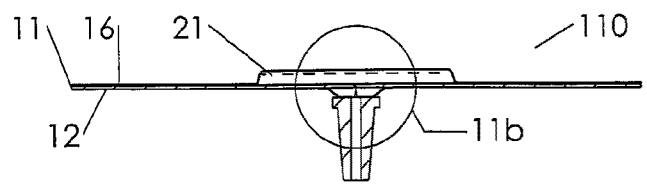
FIG. 11 illustrates a further preferred embodiment where the fluid transport device comprises a piercing member for rupturing the reservoir wall.
Figure 11B:
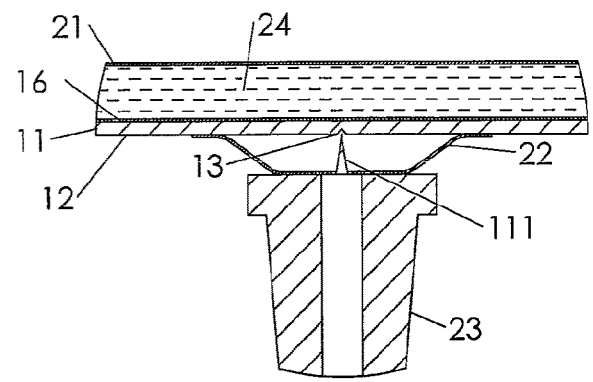
Figure 11C:
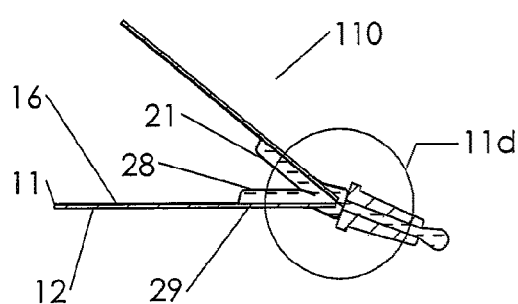
Figure 11D:
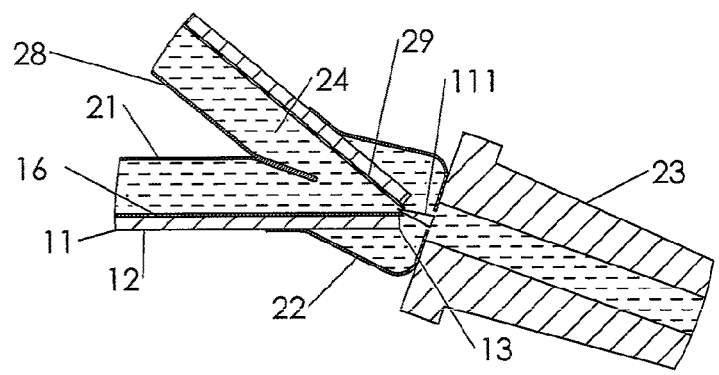

FIG. 11a and its enlarged detail in FIG. 11b illustrate a section view of a further preferred embodiment 110. The fluid transport device comprises a piercing member 111 facing the first wall 29 of the product compartment and sufficiently distant to avoid piercing the first wall 29. FIG. 11c and its enlarged detail in FIG. 11d illustrate a section view of the device after activation where the backing 11 is folded and the frangible wall section 13 is ruptured. The reconfiguration of the adapter 22 causes the fluid transport device 23 to be displaced toward the fold line 14 of the backing 11 thereby causing the piercing member 111 to rupture the first wall 29 of the product compartment 21 establishing fluid communication between the product compartment 21 and the fluid transport device 23.

In a further embodiment the frangible section is eliminated and an opening in the backing 11 allows for the member 111 to reach through during activation and rupture of the second wall 28 of the reservoir 21.

In one embodiment the backing 11 comprises an over-layer lamination to the first side 12 which covers the frangible wall section 13 as described in FIG. 1i. The piercing member 111 will rupture the lamination upon the displacement of the fluid transport device 23 upon activation as described in FIGS. 11c and 11d above.

In another embodiment the piercing member is hollow and provides a flow inlet to the fluid transport device. In another embodiment the fluid transport device is a needle and the piercing member is a sharpened back end of the needle.

FIG. 12 illustrates a further preferred embodiment where the fluid transport device is a needle 122 with a plastic hub 121 fixed to the backing 11.

Figure 12A:
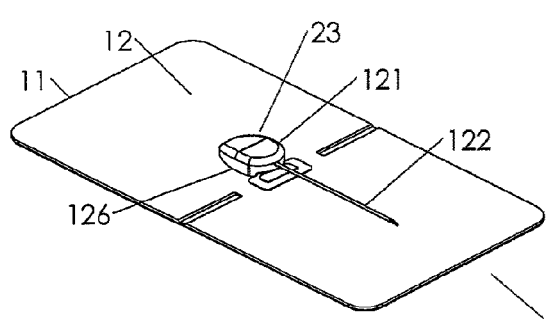
FIG. 12 illustrates a further preferred embodiment where the fluid transport device is a hypodermic needle having a hub firmly attached to the backing.
Figure 12B:
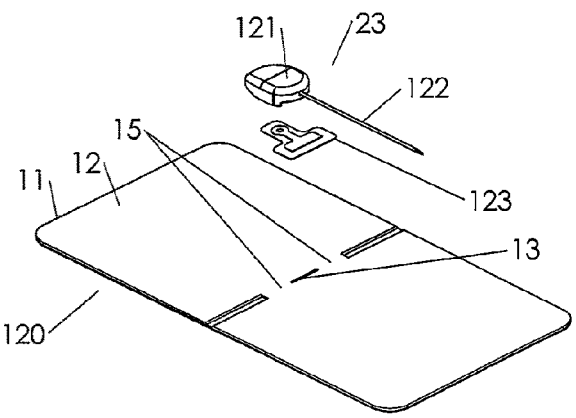

FIG. 12a illustrates the first side 12 of the backing 11 showing a fluid transport device 23, in a fashion of a hypodermic needle 122, having its proximal end attached via a hub 121 to the backing 11 in an offset position from the backing's 11 fold line 14. The needle receives some level of protection from damage or from injuring the user since it is concealed behind the backing. FIG. 12b illustrates an exploded view of the device, revealing the frangible section 13 of the backing 11 and the bordering area 15 around it. An adapter 123 is accommodated between the backing 11 and the needle hub 121.

Figure 12C:
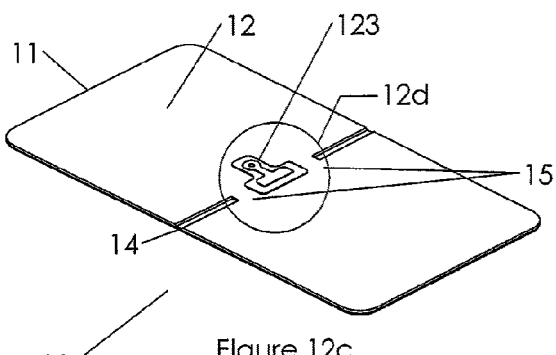
Figure 12D:
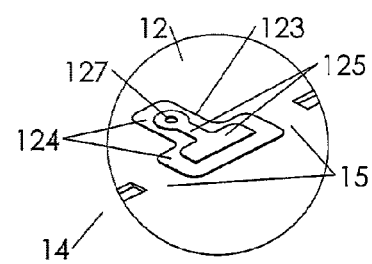

FIGS. 12c and 12d illustrate a semi assembled device where the adapter 123 is attached to the backing 11 along its circumference 124 which forms a fluid channel 125 between the frangible section 13 and an outlet opening 127 in the adapter 123 which is located at an offset position from the fold line 14.

Figure 12E:
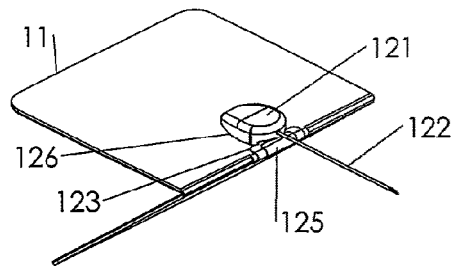

FIG. 12e illustrates the device after the backing 11 is folded which exposes the free distal end of the needle and prepares the device 120 for injection.

Figure 12F:
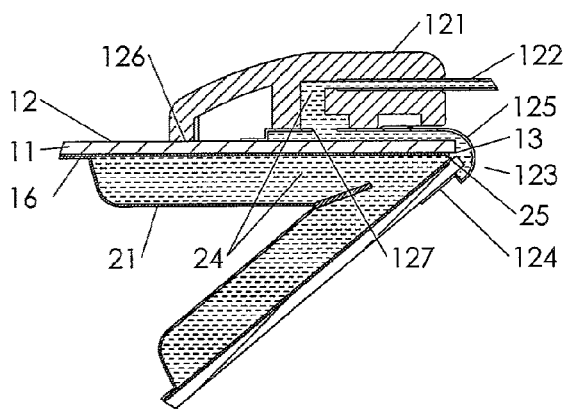

FIG. 12f illustrates a detail section view of the device 120 in the activated position showing the product 24 flowing from the product compartment 21, through the frangible wall section 13, the channel 125 in the adapter 123, and the hub 121 to the needle 122. The fluid tight attachment of the adapter 123 and the hub 121 is shown. The needle hub 121 can be attached to the backing by one of the means known in the art including gluing or welding In one embodiment a weak seal is implemented across the thin neck of the flow passage 125 which will open upon a predetermined pressure in the fluid compartment thus adding another control step before communicating the product with the needle 122.

Figures 13A, 13B:
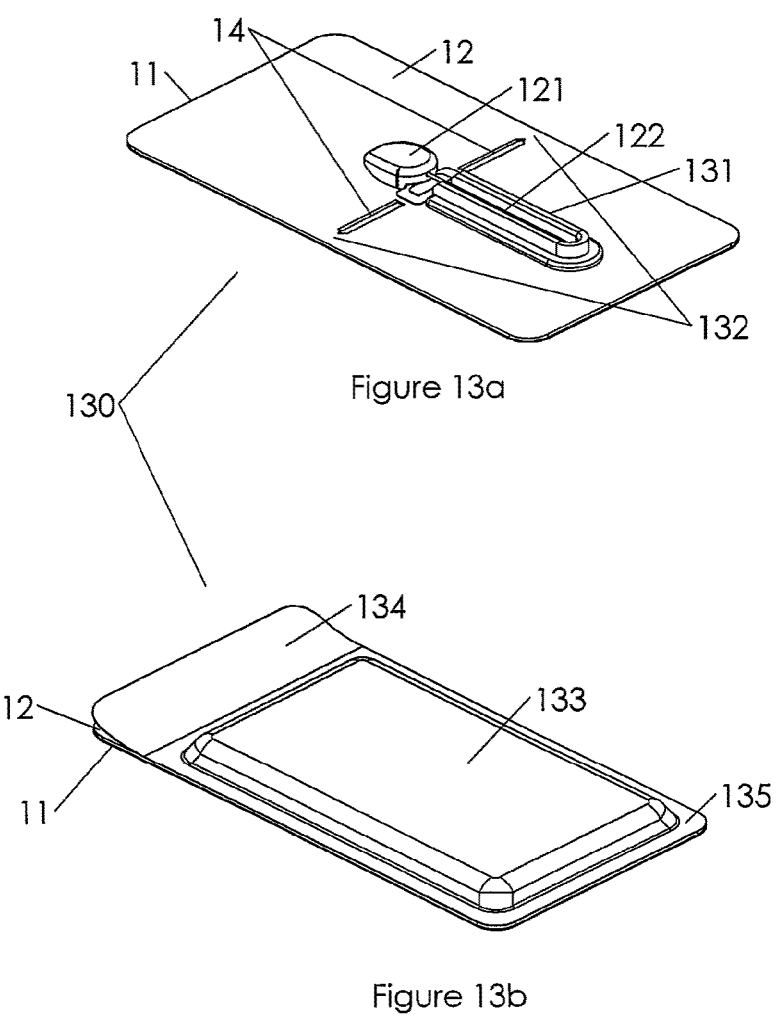
FIG. 13 illustrates a further preferred embodiment where the needle is protected by a needle protector when the backing is in the flat position.

FIG. 13 illustrates a further preferred embodiment. FIG. 13a illustrates the first side 12 of the backing 11. The living hinge in this configuration is terminated before reaching the edge of the backing 11 leaving flat surfaces 132 along the edges. The needle is now confined in a cradle 131 which is attached to the first side of the backing 11, providing another protection to and from the needle 122.

FIG. 13b illustrates the device 130 comprising a removable foil cover 133 which is attached in a sealed fashion around the circumference 135 of the backing 11, leaving a peel-away tab 134 outside the sealed section for pulling the cover 133 off. This over wrap foil forms an aseptic space around the needle to maintain its sterility until the point of use.

FIG. 14 illustrates a further preferred embodiment where the fluid transport device, in a fashion of a hypodermic needle, is firmly attached to the backing 11. FIG. 14a and its enlarged detail view in FIG. 14b shows the second side 16 of the backing 11. The needle 122 is connected to the backing 11 through a bore 141 which leads to channel 142. A recess 149 in the backing 11 provides protection to and from the needle 122. An open channel 142 starts at a through hole 143 and terminates in the needle bore 141. This channel 142 will later be covered by the first wall 129 of reservoir compartment 121, completing a closed channel with an inlet opening at hole 143 and an outlet opening at the needle bore 144.

FIG. 14c illustrates the first side 12 of the backing 11 which is mostly similar to former embodiments except for the recess 149 for accommodating the needle, and the through hole 143.

FIG. 14d illustrates a view of the second side 16 of the backing 11. The needle bore 144 is in fluid communication between the fluid channel 142 and the recess for the needle 149.

FIG. 14e illustrates an assembled device 140 in the flat position with a needle 122 immovably disposed in the bore 144 through opening 141. The needle 122 is accommodated in the recess 149 which provides needle stick protection. FIG. 14f illustrates the activated position of the device where the backing 11 is folded. The adapter 23 reconfigures to support the folded position while maintaining sealed edges to the backing 11.

FIG. 14g illustrates a detail section view at the longitudinal center line showing portions of the flow path of the product 24. The product 24 flows from the product compartment 21 through the slit 25 in the first wall 29, the ruptured frangible section 13 in the backing 11, the passage between the adapter 123 wall and the backing, and through the through hole 143 to flow channel 142. The first wall 29 of the reservoir compartment 21 seals over the flow channel 142 making it a closed channel with an inlet at through hole 143 and an outlet to the needle bore 144.

FIG. 14h is a section view at the needle centerline illustrating the flow path from the fluid channel 142, through the needle bore 144 into the needle 122.

FIG. 14i illustrates the device after the dispensing process has been completed. The backing 11 is reverse folded around the living hinge 14 in an opposite folding position to FIG. 14h. By doing so the needle 122 is bent and destroyed, and is now safely protected from causing needle sticks and/or contamination. A latch feature (not shown) will perpetually maintain the device locked in this position. The latch feature can include any means known in the art including an adhesive strip, glue, pressure activated glue, or a mechanical latch such as a snap feature.

Figure 15A:
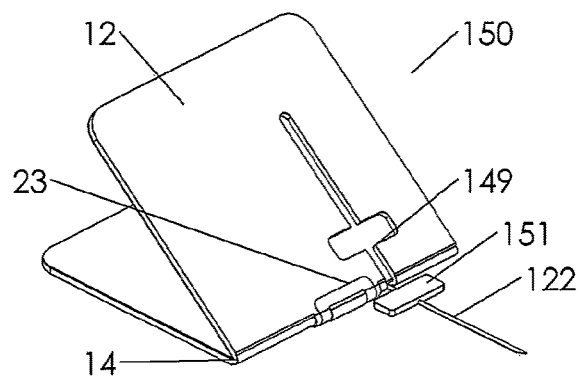
FIG. 15 illustrates a further preferred embodiment where the needle is manually retractable to rupture the frangible section of the backing.

FIG. 15a illustrates a further embodiment 150, mostly similar to the embodiment of FIG. 14. Here, the needle is movably disposed in the bore 144 and is able to axially travel within the bore 144, between a pre-administration position and an administration position. A laterally protruding part 151 is firmly attached to the needle such that when pushed toward the fold line of the backing 11 it will cause the needle to move in this direction.

Figure 15B:
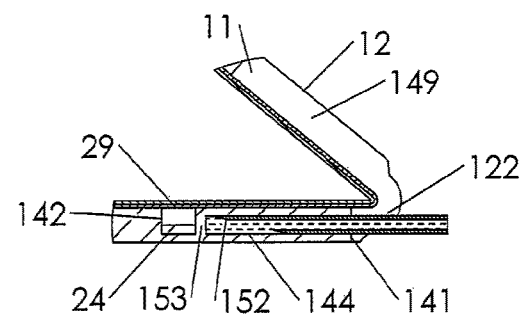

FIG. 15b is a cross section view at the needle center line of the device in the flat pre-activation position. The needle has a second sharp end 152 accommodated in the bore 144. A thin membrane 153 separates between the bore 144 and the fluid channel 142. When the needle is pushed toward the membrane 153 it will rupture the membrane and establish fluid communication between the fluid channel 142 and the needle 122. The embodiment is advantageous in some applications where better control is required regarding the instant in which the fluid may dispense from the device. In one application the laterally protruding part 151 is pushed back by the body of the patient after the needle has been completely inserted into the body ensuring that the fluid could be dispensed only after the needle is fully.

Figure 16:
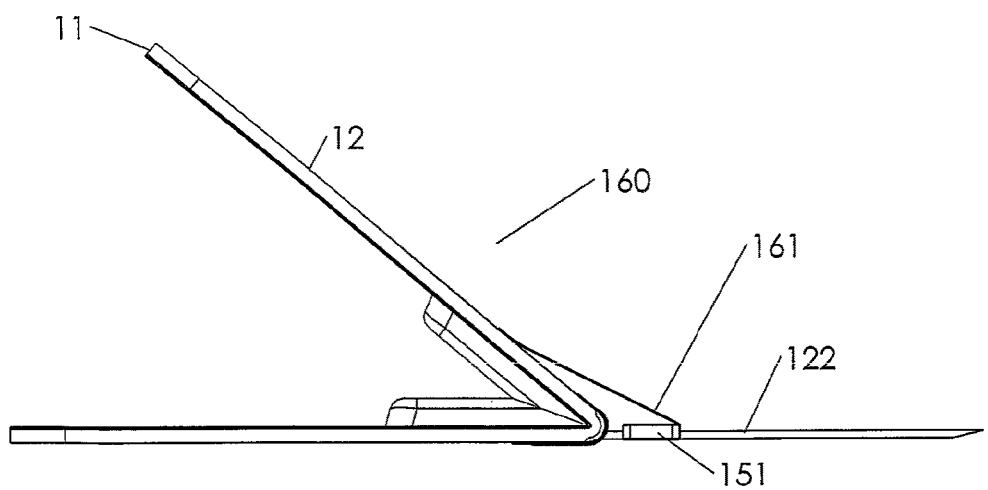
FIG. 16 illustrates a further preferred embodiment of the present invention where the needle is retractable to rupture the frangible section upon folding of the backing.

FIG. 16 illustrates a further preferred embodiment 160 with the exception that a flexible non-stretchable strip 161 connects between the first surface 12 of the backing 11 and the laterally protruding part 151 such that when the backing is folded, the laterally protruding part 151 is pulled toward the fold line of the backing 11 thereby causing the needle to rupture the membrane 153 (not shown). This embodiment is advantageous where it is desired to avoid early burst of the content 24 immediately upon cracking the frangible wall section 13.

Figure 17A:
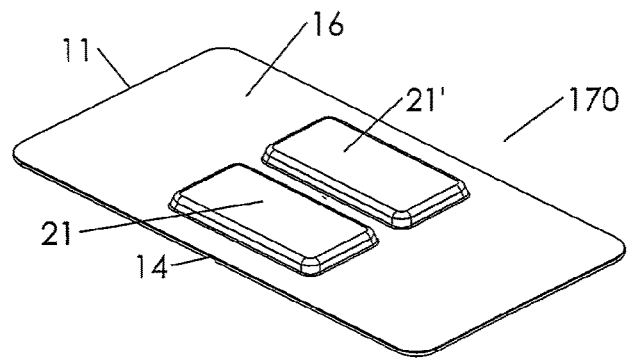
FIG. 17 illustrates a preferred embodiment comprising two reservoir compartments where the contents of said reservoirs are mixed in the adapter prior to delivery.
Figure 17B:
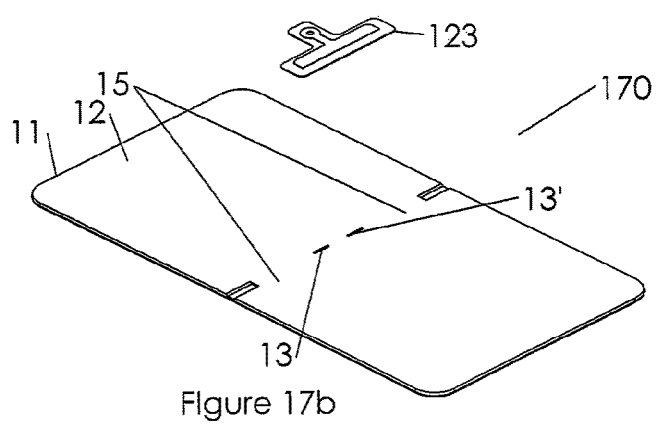
Figure 17C:
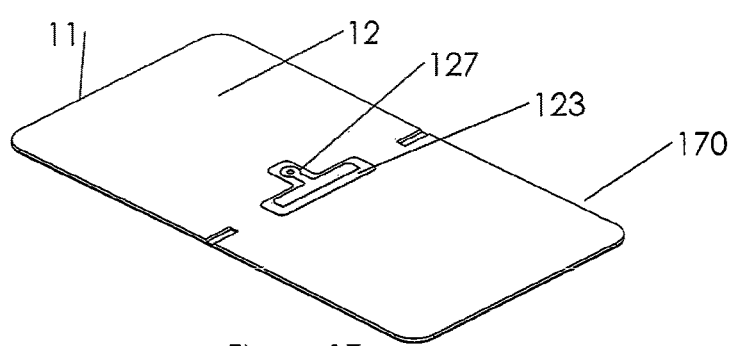

FIG. 17 illustrates a semi-finished assembly of a further embodiment 170 which comprises a plurality of reservoir compartments. Each compartment comprise its compartment rupturing mechanism as described in the preceding Figures, but the adapter channels the dispensed fluids to a common fluid transport device. FIG. 17*a* illustrates the device where the second side 16 of the backing 11 is visible with two reservoir compartments 21 and 21' accommodated on it. FIG. 17*b* shows an exploded view of a semi-finished device. The Figure exposes the frangible wall sections 13 and 13' of compartments 21 and 21' and the bordering smooth and uninterrupted area 15 around them for attaching the adapter 123. FIG. 17*c* illustrates a semi-finished device where the adapter seals to the bordering area 15 such that the frangible wall sections 13 and 13' are in fluid communication with opening 127. The flow passage between the backing 11 and the adapter 123 may further comprise a mixing element to enhance the mixture of the compounds of the compartments 21 and 21'. In one embodiment the mixing element is an insert that imposes intersecting flows and/or high shear between the two compound flows. In another embodiment the mixing element is merely the pattern in which the adapter 123 and the backing 11 are attached which causes the flow to stir, intersect, and shear.

It will be obvious to those skilled in the art that completely independent dispensing units (i.e. separate reservoir compartments and fluid transport device(s) for each compound or dose) can be implemented on a common backing.

The present invention is not limited to backings with a general shape of a credit card as illustrated in the Figures above. The backing may be constructed in any shape and form as long as it provides for one or more of the functionalities described or inherent herein.

The present invention is also not limited to reservoir compartment(s) which are limited in size to the perimeters of the backing. The reservoir may extend to any size and form as long as it is supported by the backing in a form that provides for the functionality(ies) described or inherent herein. For example, one arrangement the reservoir compartment may comprise a flexible neck having a first opening and a second opening, where the first opening terminates with a welding flange for connecting the neck to the backing in a fluid tight fashion; said second opening extending to a substantially larger reservoir compartment for holding the dispensable fluid.

Accordingly, the present invention has been described with some degree of particularity directed to the exemplary embodiments thereof. It should be appreciated, though, that the present invention is defined by the following claims construed in light of the prior art so that modifications or changes may be made to the exemplary embodiments of the present invention without departing from the inventive concepts contained herein.

What is being claimed:

1. A dispensing device, comprising:
   a backing including a frangible section adapted to at least partially open as said backing is moved from a first position toward a second position;
   at least a first product compartment disposed on said backing in confronting relationship to said frangible section;
   a fluid transport device disposed on said backing in confronting relationship to said frangible section; and
   an adapter having a proximal end portion joined with said backing and a distal end portion joined with said fluid transport device;
   wherein said adapter is constructed to bring the fluid transport device into closer proximity to the backing as the backing moves from the first position to the second position.

2. A dispensing device according to claim 1 wherein a surface region of said backing proximate to said frangible section is uninterrupted to permit said backing to accommodate an adapter.

3. A dispensing device according to claim 1 wherein said frangible section comprises a primary slit formed partially through a first surface of said backing.

4. A dispensing device according to claim 3 wherein said frangible section further comprises a travel limiter.

5. A dispensing device according to claim 4 wherein said travel limiter comprises at least one secondary slit formed partially through said first surface and extending transversely to said primary slit.

6. A dispensing device according to claim 1 wherein said backing comprises a first material and a second material, said first material defining said frangible section and having reduced structural integrity relative to said second material such that said first material cracks at least partially open upon movement of the backing from the first position toward the second position, while said second material remains intact.

7. A dispensing device according to claim 1 wherein said backing is a panel piece and includes a living hinge disposed along a fold line to separate said backing into a pair of flaps that are movable with respect to one another.

8. A dispensing device according to claim 7 wherein said living hinge is centrally located along said backing and comprises a plurality of living hinge sections each extending inwardly from a respective edge margin of said panel piece, said frangible section disposed between said living hinge sections.

9. A dispensing device according to claim 1 wherein said fluid transport device communicates with said backing through an adapter.

10. A dispensing device according to claim 1 wherein said adapter is face-sealed to said fluid transport device.

11. A dispensing device according to claim 1 wherein said adapter surrounds a portion of said fluid transport device.

12. A dispensing device according to claim 1 wherein said fluid transport device is selected from a group consisting of a spout, a connector, a fitting, a Luer Slip connector/fitting, a Luer Lock connector, a needle, a hypodermic needle, a mini-needle, a set of mini needles, a micro needle, an array of micro needles, a tube, a pipe, a spray head, an oral dropper, a nasal dropper, a nasal sprayer, an eye dropper, an eye sprayer, a topical applicator, a jet injector, an adapter to a spout, an adapter to a connector, an adapter to a fitting, an adapter to a Luer Slip connector/fitting, an adapter to a Luer Lock connector, an adapter to a needle, an adapter to a hypodermic needle, an adapter to a mini-needle, an adapter to a set of mini needles, an adapter to a micro needle, an adapter to an array of micro needles, an adapter to a tube, an adapter to a pipe, an adapter to a spray head, an adapter to an oral dropper, an adapter to a nasal dropper, an adapter to a nasal sprayer, an adapter to an eye dropper, an adapter to an eye sprayer, an adapter to a topical applicator, an adapter to a jet injector, and an adapter to an absorbent material.

13. A dispensing device according to claim 1 wherein said fluid transport device includes a hub in confronting relationship to said adapter and a hypodermic needle having a proximal end disposed in said hub and extending from said proximal end to terminate at a free distal end.

14. A dispensing device according to claim 1 further comprising a protector for said fluid transport device.

15. The dispensing device according to claim 1 wherein said backing at least partially protects a portion of said fluid transport device when in the first position and exposes at least a portion of said fluid transport device when in the second position.

16. A dispensing device according to claim 1 further comprising a removable cover disposed on said backing and protecting said fluid transport device, said cover including a peel-away tab.

17. A dispensing device according to claim 1 wherein said fluid transport device is immovably disposed in said backing.

18. A dispensing device according to claim 1 wherein said fluid transport device is movably disposed in said backing between a pre-administration position and an administration position.

19. A dispensing device according to claim 1 comprising a plurality of fluid compartments and at least one mixing seal disposed therebetween.

20. A dispensing device according to claim 19 wherein said mixing seal is aligned in confronting relationship to the frangible section of said backing.

21. A dispensing device according to claim 19 wherein said mixing seal is offset from the frangible section of said backing.

22. A dispensing device according to claim 19 further comprising an adapter channeling contents of said compartments into said fluid transport device upon rupture of said frangible section.

23. A dispensing device according to claim 1 wherein said backing has a fold line and said first fluid compartment is offset from the fold line.

24. The dispensing device according to claim 1 where said adapter is constructed to reduce flexibility between the fluid transport device and the backing as the backing moves from the first position to the second position.

25. A dispensing device according to claim 1 wherein said fluid transport device includes a piercing element directed toward said frangible section such that, when said backing is in said first position, said piercing element is spaced apart from said frangible section, and when said backing is moved from the first position toward the second position, said piercing element penetrates said frangible section to establish fluid communication between said first product compartment and said dispensing device.

26. A dispensing device of claim 1 where said frangible section and said fluid transport device communicate through a fluid passageway at least partially disposed or formed: between two walls of the product compartments, between the product compartments and the backing, or in the backing.

27. A dispensing device according to claim 1 wherein:
said backing comprises a rectangular panel piece that includes a fold line separating said backing into a first flap and a second flap, said second flap defining a compression panel;
said frangible section is disposed along said fold line and adapted to break open as said backing is moved from the first position toward the second position;
said at least a first product compartment is disposed in confronting relationship to said frangible section on said first flap on a first side of said backing;
said adapter is disposed on a second side of said backing in confronting relationship to said frangible section; and
said fluid transport device is joined to said adapter such that, as said backing moves from the first position toward the second position, said compression panel compresses said first product compartment causing its content to be channeled by said adapter into said fluid transport device.

28. A method comprising:
a) providing a dispensing device comprising:
a backing movable from a first position toward a second position;
at least a first product compartment disposed on said backing; and
a fluid transport device adapted to be placed in fluid communication with said first product compartment;
b) moving the backing from the first position toward the second position to compress said first product compartment and cause its content to be dispensed through said fluid transport device; and
c) drawing the fluid transport device toward said backing as said backing moves from the first position toward the second position, thereby to reduce the flexibility between the fluid transport device and said backing.

29. A dispensing device, comprising:
a backing including a frangible section adapted to at least partially open as said backing is moved from a first position toward a second position;
at least a first product compartment disposed on said backing in confronting relationship to said frangible section;
a fluid transport device disposed on said backing in confronting relationship to said frangible section; and
an adapter having a proximal end portion joined with said backing and a distal end portion joined with said fluid transport device;
where said adapter is constructed to reduce flexibility between the fluid transport device and the backing as the backing moves from the first position to the second position.

* * * * *